(12) United States Patent
van't Hooft

(10) Patent No.: US 7,871,365 B2
(45) Date of Patent: Jan. 18, 2011

(54) GYNECOLOGICAL INSTRUMENT

(75) Inventor: Eric van't Hooft, Brasschaat (BE)

(73) Assignee: Isodose Control Intellectual Property, B.V., Veenendaal (NL)

( * ) Notice: Subject to any disclaimer, the term of this patent is extended or adjusted under 35 U.S.C. 154(b) by 496 days.

(21) Appl. No.: 11/746,983

(22) Filed: May 10, 2007

(65) Prior Publication Data

US 2007/0276177 A1  Nov. 29, 2007

(30) Foreign Application Priority Data

May 10, 2006  (NL) .................................. 1031785

(51) Int. Cl.
*A61N 5/00* (2006.01)
(52) U.S. Cl. ............................................. 600/6; 600/3
(58) Field of Classification Search .................. 600/1–8, 600/33–35; 128/830–841; 604/20–21, 96.01, 604/101.01, 101.04, 103, 103.03, 117, 164.01–167.07, 604/271, 279, 285, 514, 515, 523, 533–539; 606/108, 192–194
See application file for complete search history.

(56) References Cited

U.S. PATENT DOCUMENTS 3,323,511 A  *  6/1967  Holter .......................... 600/6
3,807,386 A       4/1974  Rocoplan et al.
4,294,264 A  * 10/1981  Fischell et al. .............. 600/591
5,562,594 A      10/1996  Weeks
6,390,968 B1     5/2002  Harmon

FOREIGN PATENT DOCUMENTS

DE    44 13 489 C1    8/1995
DE    44 13 491 C1    8/1995

OTHER PUBLICATIONS

International Search Report for NL 1031785.

* cited by examiner

*Primary Examiner*—Charles A Marmor, II
*Assistant Examiner*—Carrie Dorna
(74) *Attorney, Agent, or Firm*—Leydig, Voit & Mayer, Ltd.

(57) ABSTRACT

An apparatus is described for irradiating cervical cancer, comprising multiple source guide tubes with a coupling piece situated outside the patient that connects the tubes outside the patient. The source guide tubes are formed such that the portions of the tubes situated in the patient upon insertion hook to each other so that the tubes are locked relative to each other. In an embodiment, the apparatus further comprises a central catheter tube to be guided into the uterus, which is provided with a flange-shaped stop for stabilizing the central tube relative to the uterus, the stop being formed for securing a position of the central tube relative to the further source guide tubes.

2 Claims, 5 Drawing Sheets

GYNECOLOGICAL INSTRUMENT

FIELD OF THE INVENTION

The invention relates to a gynecological instrument for introducing an irradiation catheter. In particular, the invention relates to a tubular applicator for irradiating gynecological tumors, which is to be placed in the cervix and the bottom of the vagina.

BACKGROUND

DE4413489 shows an instrument for irradiating gynecological tumors where irradiation positions are realized by a central catheter which is introduced into the uterus, and two laterally pivotable catheters at whose ends the so-called ovoids have been provided and which are pressed against the cervix, are pushed apart at the front of the cervix. The applicator can be connected to a so-called remote afterloading machine which, via tubes, moves a radioactive source to an irradiation position in the tubes. The applicator usually comprises multiple tubes with two ovoids (egg-shaped spacers) on the two outer tubes, which ensure that the irradiation doses on the surface remain below the permissible limit. Alternatively, a so-called ring applicator tube can be used, whereby around the cervix a ring-shaped tube is applied in which a radioactive source can be moved and a dosed radiation delivery is possible. Irradiation is performed by bringing a radiation source, provided at the end of a guide cable via a guide tube and the catheter, in a desired position and allowing it to deliver radiation there for a predetermined length of time to attack the tumor.

Such applicators are often too large to allow insertion in an assembled condition and are therefore provided tube by tube and fixed by means of a screw clamp. Additionally, then, in the apparatus, in the direction of the large intestine and in the direction of the bladder, the interspace is stuffed with gauze. This is a laborious process and possibly painful and uncomfortable and often done under anesthesia which moreover is carried out differently by different doctors, which may adversely affect the success of the medical procedure.

This method accordingly has disadvantages associated with it because it depends on the skills of the medical staff whether it will yield an optimum result. Because the positioning of the central intrauterine tube and other tubes (in particular the colpostats or the ring applicator tube) may shift relative to each other, this entails risks for the patient, also because the bladder and the large intestine may thus be exposed to excessive radiation.

SUMMARY OF THE INVENTION

It is an object of the invention to provide an instrument where these disadvantages are obviated and where the catheters can be easily held at a uniform distance from each other, without the catheters being able to shift relative to each other during a treatment. At the same time, it is an object of the invention to provide an instrument which can be introduced quickly and with a minimal burden and whose positioning is accurate and reliable.

This object is achieved by an apparatus for irradiating cervical cancer, comprising multiple source guide tubes with a coupling piece situated outside the patient which connects the tubes outside the patient, characterized in that the source guide tubes are formed such that the portions of the tubes situated in the patient upon insertion hook to each other so that the tubes are fixated relative to each other.

BRIEF DESCRIPTION OF THE DRAWINGS

The invention will be elucidated in more detail in and by a description of the drawings, in which.

DETAILED DESCRIPTION OF THE DRAWINGS

Figure 1:
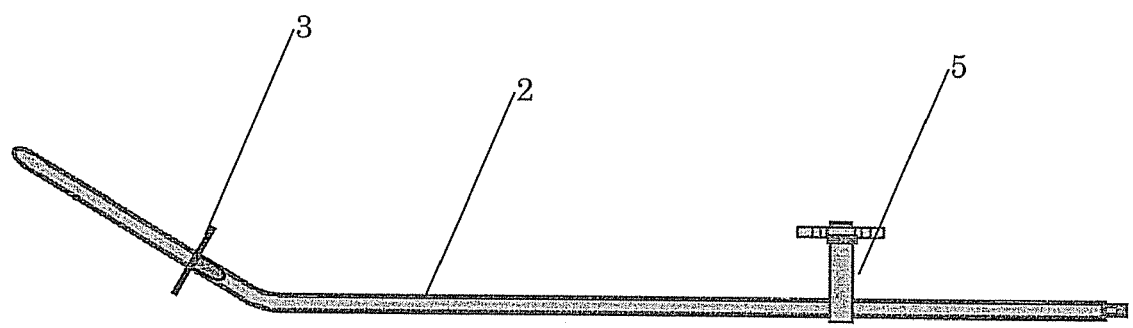
FIG. 1 shows a side elevational view of a central catheter tube, provided with a positioning means according to the invention.

In the drawings, the same or corresponding parts are designated by the same reference numerals.

Figure 2:
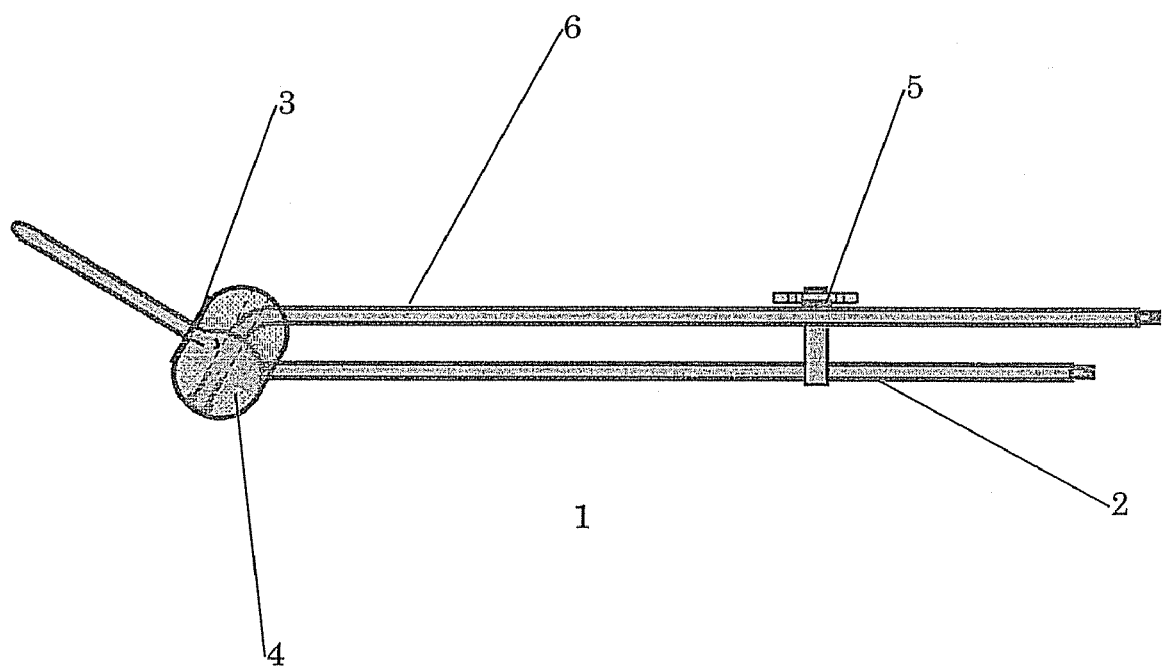
FIG. 2 shows a side elevation of the central catheter tube, provided with a positioning means according to the invention and a colpostat, which is fixated by the positioning means.

FIG. 1 shows a side elevational view of a (part of a) gynecological applicator 1 to be inserted in the vagina against and into the cervix. Shown in particular is a central catheter tube 2 (also named intrauterine tube), provided with a positioning means. The positioning means comprises in the exemplary embodiment a central flange-shaped stop 3, also named cervical flange, which has been adapted according to the invention. The stop 3 serves to abut, during radiation, against the cervix, in some cases against a ring-shaped element (not shown, so-called Smith sleeve) which may be fixedly attached on the cervix to effect a reproducible fixation of the applicator 1. The central catheter tube 2 accordingly serves for insertion into the cervix for intrauterine irradiation. FIG. 2 shows a side elevational view of the applicator 1 as in FIG. 1.

As shown in FIG. 2, the applicator 1 in the exemplary embodiment comprises two plastic ovoid structures or colpostats 4 (see also FIG. 3 and FIG. 4), which are combined with the intrauterine tube 2, so that after placement, during the irradiation, a high dose can be delivered to the base of the uterus without the ambient tissue such as large intestine and bladder needing to be burdened unduly heavily.

Preventing this excessive burdening is of major importance since otherwise serious complications may be expected. Owing to the makeup of this model of applicator (with colpostats), typically a construction is used which, to save weight, utilizes thin tubes, with the tubes blocked on the rear side as represented in FIG. 1 and FIG. 2. To that end, the apparatus comprises a coupling piece 5 situated outside the patient, for instance a clamp or screw, which connects the tubes, in particular the intrauterine tube 2 and the tube 6 of the colpostat 4 outside the patient and keeps them in position. Accordingly, an apparatus is shown that comprises a plurality of source guide tube members 2, 6 and having a first coupling piece 5 connected to a central tube 2. The coupling piece 5 couples to the other tube member 6 and is arranged outside the patient in use.

In addition, according to the invention, therefore, the source guide tubes 2 are formed such that the portions of the tubes situated in the patient upon insertion hook to each other by means of a coupling piece (stop 3) connected to the central tube 2 in the form of stop 3, so that the tubes 2 and 6 (see FIG. 2) are locked relative to each other. In particular, the stop 3 fixates the ovoid structures 4. In this way, the stop 3 is formed having protrusions 7 (see FIGS. 3 and 4) for insertion in a corresponding insertion opening 8 formed the ovoid structures 4 of the other guide tube member 6 to couple the guide tube members 2 and 6 to each other inside the patient.

Figure 3:
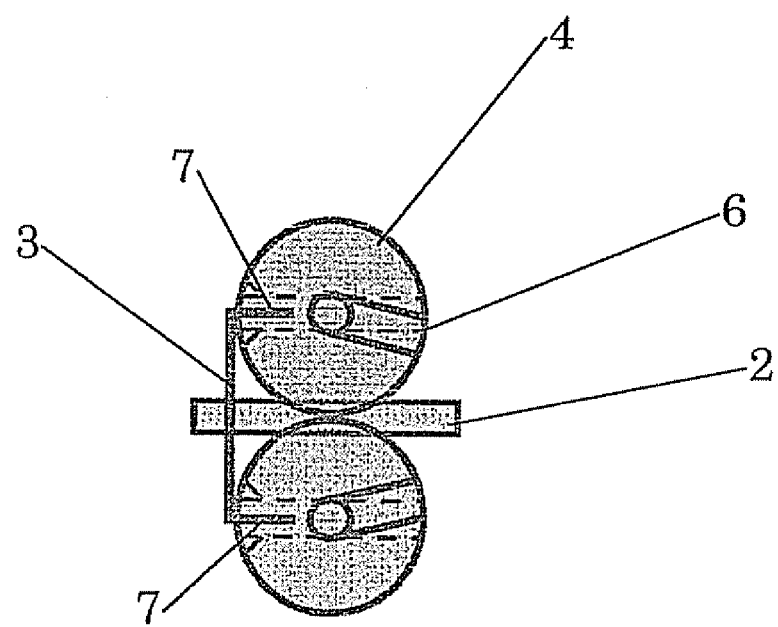
FIG. 3 shows a top plan view of the configuration of FIG. 2.
Figure 4:
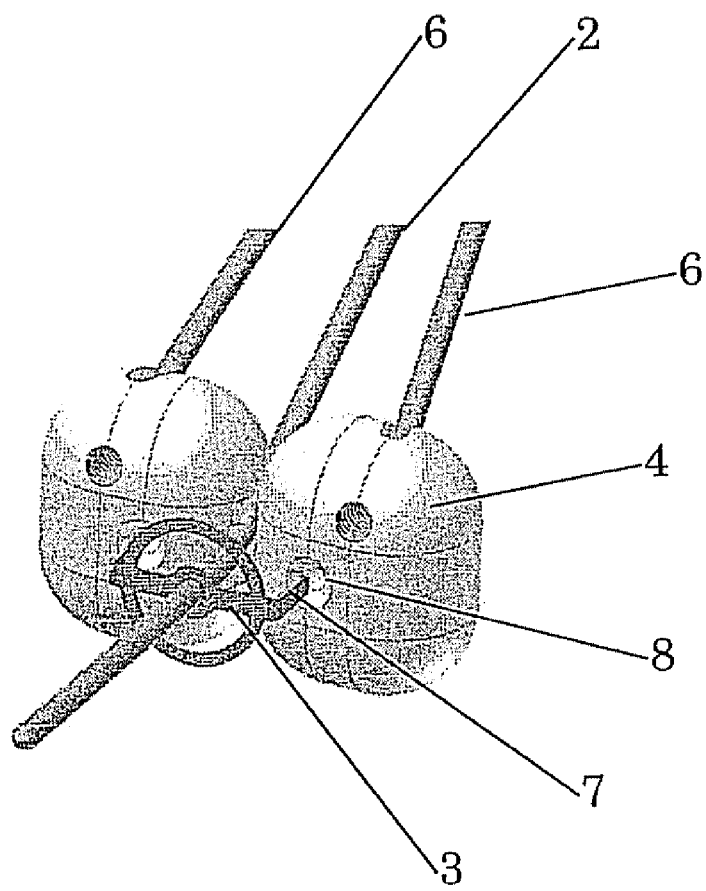
FIG. 4 shows a schematic perspective front view of the configuration of FIG. 2.

FIG. 3 and FIG. 4 show a top plan view and a perspective front view, respectively, of the ovoid structures 4 which are arranged next to a central stop 3. Specifically, the applicator comprises two ovoid structures 4 on respective tubes 6 arranged on opposite sides of the central tube 2. It is shown in particular that the stop 3 is designed with two projections 7 each falling into a corresponding opening 8 of an ovoid structure 4. Accordingly the stopper 3 stabilizes the central tube 2 relative to the uterus and meanwhile secures a position of the other source tube 6 relative to the central tube 2 that is movable away from the central catheter tube 2.

During so-called tamponing (pushing away of bladder and rectum) of the tissue around the colpostat, the colpostats are pressed from their set position so that the radiation dose to be given changes unintentionally. This can entail serious errors in the dose distribution. The provision of two anchor pins on the cervical flange which anchor themselves in pre-drilled holes in the colpostats solves the problem of unwanted position change.

Figure 5:
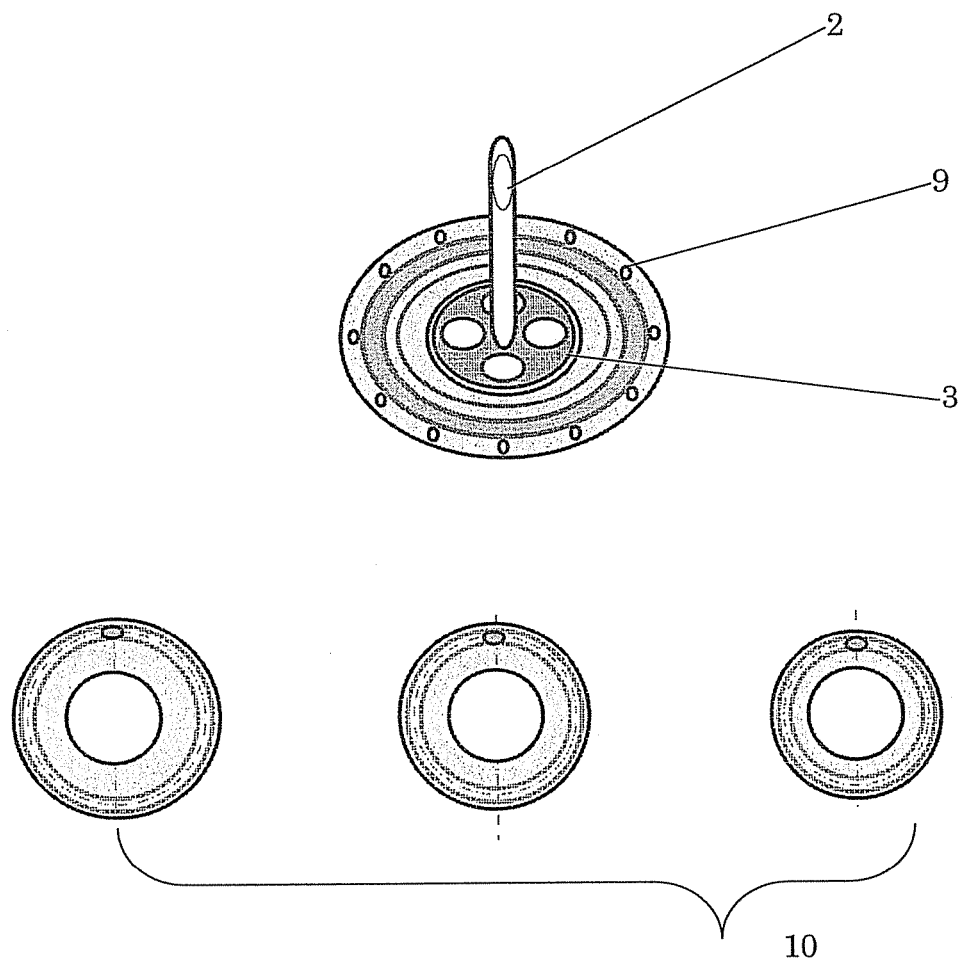
FIG. 5 shows a schematic perspective view of a positioning means for a ring applicator.

Finally, FIG. 5 schematically shows a second embodiment in which the source guide tubes comprise a ring applicator tube 9, of different dimensions 10. The flange-shaped stopping means (e.g., stop 3) is arranged for insertion into the central opening of the ring applicator tube 9 and thus fixates the ring applicator tube 9 relative to the intrauterine tube 2. The conventional stop does not do this and only serves for axial positioning of the intrauterine tube 2.

Although the invention has been elucidated with reference to the examples shown in the drawings, the invention is not limited thereto but may also comprise variations or modifications without deviating from the spirit of the invention. The scope of the invention is determined by the following claims.

What is claimed is:

1. An apparatus for irradiating cervical cancer, comprising: two source guide tube members;
a first coupling piece connected to a first source guide tube member, to be situated outside a patient for coupling to a second guide tube member outside the patient,
a second coupling piece connected to the first source guide tube member, for coupling to the second source guide tube member, the second coupling piece arranged to be situated inside the patient;
wherein the second coupling piece is formed as an insert for insertion in a corresponding insertion opening formed in the second guide tube member; so as to couple first and second guide tube members relative to each other inside the patient;
further comprising a central catheter tube to be guided into the uterus,
wherein the second coupling piece is formed by a flange-shaped stop provided on the central catheter tube for stabilizing the central tube relative to the uterus, the stop being formed for securing a position of the central tube relative to the further source guide tubes,
wherein the source guide tubes comprise two ovoid structures movable out of the center,
wherein the center is defined by the central catheter tube, and
wherein the stop is designed with two projections each falling into a corresponding opening of an ovoid structure.

2. An apparatus for irradiating cervical cancer, comprising: two source guide tube members;
a first coupling piece connected to a first source guide tube member, to be situated outside a patient for coupling to a second guide tube member outside the patient,
a second coupling piece connected to the first source guide tube member, for coupling to the first source guide tube member, the second coupling piece arranged to be situated inside the patient;
wherein the second coupling piece is formed as an insert for insertion in a corresponding insertion opening formed in the second guide tube member; so as to couple first and second guide tube members relative to each other inside the patient;
further comprising a central catheter tube to be guided into the uterus, wherein the second coupling piece is formed by a flange-shaped stop provided on the central catheter tube for stabilizing the central tube relative to the uterus, the stop being formed for securing a position of the central tube relative to the further source guide tubes,
wherein the source guide tubes comprise a ring applicator tube and wherein the flange-shaped stop falls into a central opening of a ring applicator tube.

* * * * *